(12) United States Patent
Hsu et al.

(10) Patent No.: US 8,702,960 B2
(45) Date of Patent: Apr. 22, 2014

(54) METHOD FOR OPERATING A MEASUREMENT FOR A SAMPLE ON AN ELECTROCHEMICAL TEST STRIP

(75) Inventors: Cheng-Teng Hsu, Taichung (TW); Chun-Wei Su, Taichung (TW); Chieh-Hsing Chen, Changhua County (TW)

(73) Assignee: Bionime Corporation, Taichung (TW)

( * ) Notice: Subject to any disclaimer, the term of this patent is extended or adjusted under 35 U.S.C. 154(b) by 111 days.

(21) Appl. No.: 13/252,973

(22) Filed: Oct. 4, 2011

(65) Prior Publication Data
US 2013/0008802 A1 Jan. 10, 2013

(30) Foreign Application Priority Data

Jul. 6, 2011 (TW) .............................. 100123959 A

(51) Int. Cl.
*G01N 27/26* (2006.01)
*G01N 33/487* (2006.01)

(52) U.S. Cl.
USPC ..... 205/777.5; 205/775; 205/792; 204/403.1; 422/68.1; 422/82.01; 435/287.1; 600/347

(58) Field of Classification Search
USPC .............................. 205/775, 777.5, 778, 792; 204/403.01–403.15; 600/345–348; 422/68.1, 82.01; 435/287.1, 287.2
See application file for complete search history.

(56) References Cited

U.S. PATENT DOCUMENTS

| | | |
|---|---|---|
| 4,224,125 A | 9/1980 | Nakamura et al. |
| 5,108,564 A | 4/1992 | Szuminsky et al. |
| 5,266,179 A | 11/1993 | Nankai et al. |
| 5,352,351 A | 10/1994 | White et al. |
| 5,366,609 A | 11/1994 | White et al. |
| 5,653,863 A * | 8/1997 | Genshaw et al. .......... 205/777.5 |
| 2005/0114062 A1* | 5/2005 | Davies et al. ................. 702/104 |
| 2007/0272564 A1* | 11/2007 | Huang ..................... 204/403.01 |

FOREIGN PATENT DOCUMENTS

| | | |
|---|---|---|
| EP | 1 272 833 B1 | 11/2004 |
| TW | I334026 | 12/2010 |

\* cited by examiner

*Primary Examiner* — Jennifer Dieterle
(74) *Attorney, Agent, or Firm* — Haverstock & Owens LLP

(57) ABSTRACT

A method for operating a measurement for a sample on an electrochemical test strip including at least two electrodes is provided. The method includes steps of applying a first voltage between the two electrodes during an interference-removal period after an incubation period succeeding a moment when the sample is detected, and applying a second voltage between the two electrodes during a test period, wherein the first voltage is larger than the second voltage, the first voltage includes one of a first fixed voltage and a first set of plural pulse voltages, and the second voltage includes a second fixed voltage.

6 Claims, 14 Drawing Sheets

Applying a first voltage between the two electrodes during an interference-removal period after an incubation period succeeding a moment when the sample is detected. — 71

Applying a second voltage between the two electrodes during a test period, wherein the first voltage is larger than the second voltage the first voltage can be a fixed voltage or a set of plural pulse voltages, and the second voltage can be a fixed voltage. — 72

Fig. 7

METHOD FOR OPERATING A MEASUREMENT FOR A SAMPLE ON AN ELECTROCHEMICAL TEST STRIP

CROSS REFERENCE TO RELATED APPLICATIONS

The application claims the benefit of Taiwan Patent Application No. 100123959, filed on Jul. 6, 2011, at the Taiwan Intellectual Property Office, the disclosures of which are incorporated herein in their entirety by reference.

FIELD OF THE INVENTION

The present invention relates to a method for operating a measurement, especially to a method for operating a measurement for a sample on an electrochemical test strip.

BACKGROUND OF THE INVENTION

Electrical sensor systems are widely applied to the analyses and measurements of the analytes in biological samples, e.g. glucose concentration, cholesterol concentration, etc. in the blood. Generally, this kind of electrochemical measuring systems includes a test strip and a meter. In particular, the test strip is designed for single-time usage and is disposable for the convenience in home life.

So far several generations of the methods for analyzing and measuring the glucose concentration in a blood sample have been developed. However, general glucose concentration meters use glucose oxidase enzymes (GOD) and mediators. Typically, the mediator is potassium ferricyanide. In the test strip with the mediator, the mechanisms for the reactions among the glucose in a sample, the GOD and the mediator and the subsequent testing reactions are listed as follows.

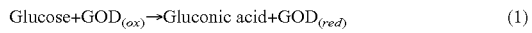

$$\text{Glucose} + \text{GOD}_{(ox)} \rightarrow \text{Gluconic acid} + \text{GOD}_{(red)} \quad (1)$$

$$\text{GOD}_{(red)} + 2M_{(ox)} \rightarrow 2M_{(red)} + \text{GOD}_{(ox)} + 2H^+ \quad (2)$$

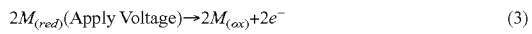

$$2M_{(red)}(\text{Apply Voltage}) \rightarrow 2M_{(ox)} + 2e^- \quad (3)$$

In the above chemical equations, $M_{(ox)}$ represents the mediator in an oxidation state and $M_{(red)}$ represents the mediator in a reduction state. The same representation way is adopted for the GOD. As shown in the above equations (1)-(3), the glucose is oxidized by the $\text{GOD}_{(ox)}$, the electron is transferred to the $\text{GOD}_{(ox)}$, and the $\text{GOD}_{(ox)}$ receives the electron and then is transformed into $\text{GOD}_{(red)}$. Next, the reduced $\text{GOD}_{(red)}$ transfers the electron to the $M_{(ox)}$, that is, the $M_{(ox)}$ is reduced into $M_{(red)}$, which is diffused to the surface of the electrode. Under the application of a fixed voltage, electronic signals are interchanged between the $M_{(red)}$ and the electrode, i.e. an electrochemical oxidation-reduction reaction. In such recirculation reactions, a sensed electrical current is generated and is proportional to the glucose concentration in the blood sample.

As the concentration of the analyte in the sample is measured by sensing the electrical current, the sensed electrical current is called Cottrell current according to the following equation:

$$i(t) = K\, n\, F\, A\, C\, D^{0.5}\, t^{-0.5}$$

where i is an instant value of the sensed current;
K is a constant;
n is the transferred electron number (For example, n is equal to 2 in the equation (3));
F is the Faraday constant;
A is the surface area of the working electrode;
C is the concentration of the analyte in the sample;
D is the diffusion coefficient of the reagent;
t is a specific time period, during which a predetermined voltage is applied to the electrodes.

The concentration C of the analyte is to be determined. This concentration is proportional to the sensed current i. Because the sensed current is also proportional to the surface area A of the working electrode, a precisely determined surface area of the working electrode of the test strip is a key factor for accurate measurements.

In additions, as shown in the Cottrell Equation, the time-dependent sensed current decreases with the square root of the time period, during which the predetermined voltage is applied to the electrodes. Therefore, the time point when a voltage is applied to the electrodes for the control of the instant measurement of the Cottrell current is another important factor for accurate measurements.

Some examples of such sensors and meters are disclosed in the patents of U.S. Pat. No. 5,266,179, U.S. Pat. No. 5,366,609 or EP 1 272 833.

The operation methods for the meters disclosed in these patents are approximately the same. First, a test strip is inserted into a meter. A proper insertion of the test strip into the meter is detected by mechanical and/or electrical switches or contacts. Once a test strip is properly inserted into the meter, the user is requested to provide a sample, typically a drop of the user's blood. The blood sample then enters a reaction zone on the test strip. The reaction zone of the test strip has at least two electrodes, which are covered by the reagent.

A drawback of the conventional meter is related to the issue of detecting the presence of the sample. In a sample presence detection period, a voltage is applied to the electrodes to detect whether the sample exists in the reaction zone. However this voltage causes the consumption of the electrical current, i.e. the consumption of the electrons, and this electrical current is generated by the reaction between the reagent and the sample. The consumed electrical current is relevant to the concentration of the analyte in the sample. Thus, the consumed current in the sample presence detection period for checking the sample presence results in a deviation on the measurement. Specially, when the volume of the sample is small or the measuring time is short, the issue of the consumption of the electrical current becomes serious.

Once the sample with sufficient volume exists in the reaction zone, the sample and the reagent are mixed in a specific time period in a second step. This specific time period is called an incubation period. After the incubation is finished, the measurement proceeds in a third step in a time period called test period.

Another issue for the conventional meters is related to the incubation period. The incubation period is afforded to allow the mixing and dissolving between the sample and the reagent, and a specific time period is required to complete these mixing and dissolving. The complete dissolution is affected by some parameters, e.g. the room temperature and the condition of the blood sample. For example, the dissolving becomes slow, when the room temperature is low or the fat concentration in the blood sample is high. If the measurement proceeds before the dissolution is completed, the instable sensed current will be generated. Thus, the incubation period must be sufficient for the longest time of the dissolution to make sure that the accurate measurement can be attained in all conditions.

If a voltage is applied during the incubation period, the electrical current is consumed during the incubation period. Since the dissolution conditions are varied from time to time, the consumed quantity of the electrical current is not stable. Thus, the application of the voltage during the incubation period would result in some deviations on the measurement. On the other hand, if no voltage is applied during the incubation period, longer time is required to reach the complete mixing and dissolving between the sample and the reagent, and meanwhile the accuracy of the measurement may be influenced by the oxygen interference, though the consumption of the electrical current during the incubation period can be avoided.

In the conventional method for operating the voltages to measure the blood sugar in U.S. Pat. No. 4,224,125, when a sample enters into a measuring device, a predetermined voltage is applied to the electrodes, and then the relationship of the steady current and the concentration is measured without power-off. Although the method without power-off can effectively aid the dissolution between the sample and the reagent, meanwhile more electrical current is consumed. Thus, the reaction strength of the analyte cannot be accumulated, the signal strength is reduced, and then the deviations of the measurement occur.

Besides, it is disclosed in the U.S. patents of U.S. Pat. No. 5,108,564 and U.S. Pat. No. 5,352,351 that if no voltage is applied in an open circuit during the incubation period, though the consumption of the electrical current can be avoided, but the oxygen bubbles inside the sample are generated and aggregated on the surface of the electrodes, the effective working area of the electrode is reduced to affect the accuracy of the measurement, and longer time is required to reach the complete mixing and dissolving between the sample and the reagent. Another drawback of the conventional meters is related to the issue of the existence of the interference material in the electrochemical test strip. The interference material, e.g. uric acid, vitamin C (ascorbic acid), acetaminophen, other in vivo metabolic materials, or in vitro introduced materials, can affect the measurement results of the blood sugar or other analytes. The US patent with U.S. Pat. No. 5,653,863 discloses a method of the voltage application as: (1) when the sample enters the meter, the positive voltage, called burn-off pulse, is applied between the two electrodes for 1-15 seconds at the voltage of 0.1-0.9 volt to reduce the background deviation; (2) in a delay period for 10-40 seconds, it is instantly powered off in an open circuit state to interrupt the electrochemical oxidation-reduction reaction; (3) the read pulse is provided to measure the concentration of the analytes. When the sample enters the meter, the application of the burn-off voltage for a long time can reduce the background interference. However, the application of the burn-off voltage also causes more consumption of the electrical current. Although it is powered off in the incubation period to reduce the current consumption, longer time is required to reach the complete mixing and dissolving between the sample and the reagent, and meanwhile the oxygen interference may occur to result in the deviations of the measurement.

For solving the above drawbacks of the conventional techniques, the Taiwan patent with the patent No. I334026 discloses an operation method for the meter, wherein series of pulses are applied to the electrodes of the test strip during both the sample detection period and incubation period so as to reduce the current consumption, to eliminate the generation of the oxygen bubbles, to effectively aid the mixing between the sample and the reagent, to shorten the mixing time and to raise the accuracy of the measurement. In this patent, the maximum value of the voltage applied during the incubation period is high enough to oxidize the mediator in the reagent on the test strip from a reduction state into an oxidation state, and low enough to avoid oxidizing the hydrogen peroxide, but is not high enough to oxidize the interference materials in the sample.

As known from the above mentioned conventional techniques, the accuracy for the relationship between the electrical current and the concentration of the analyte is not satisfied and needs to be raised. The present invention provides methods for operating the measurements to reduce the current consumption, to eliminate the oxygen interference, to sustain the steady and accurate working area of the electrodes and to largely enhance the accuracy of the measurement result. The present invention introduces the application of the voltage during an interference-removal period so that the measured current during the test period after the interference-removal period would not be affected by the interference materials in order to significantly raise the accuracy of the measurement and to overcome the issues occurring in the convention techniques, and the accurate measurement results for the analyte can be successfully obtained in spite of small volume of the sample and/or short measuring time.

SUMMARY OF THE INVENTION

The present invention introduces the application of the voltage during an interference-removal period so that the measured current during the test period after the interference-removal period would not be interfered by the interference materials in order to significantly raise the accuracy of the measurement.

In accordance with one aspect of the present invention, a method for operating a measurement for a sample on an electrochemical test strip including at least two electrodes is provided. The method includes steps of applying a first voltage between the two electrodes during an interference-removal period after an incubation period succeeding a moment when the sample is detected, and applying a second voltage between the two electrodes during a test period, wherein the first voltage is larger than the second voltage, the first voltage includes one of a first fixed voltage and a first set of plural pulse voltages, and the second voltage includes a second fixed voltage.

In accordance with another aspect of the present invention, a method for operating a measurement for a sample on an electrochemical test strip is provided, wherein the sample includes an interference material and an analyte concentration. The method includes steps of providing the electrochemical test strip; oxidizing the interference material after a first time period succeeding a moment when the electrochemical test strip is detected to have the sample thereon; and measuring the analyte concentration.

In accordance with a further aspect of the present invention, a method for operating a measurement for a sample on an electrochemical test strip including at least two electrodes is provided. The method includes steps of treating the sample by a first voltage; and measuring an electrical parameter of the sample by a second voltage, wherein the second voltage is lower than the first voltage.

The above objects and advantages of the present invention will become more readily apparent to those ordinarily skilled in the art after reviewing the following detailed descriptions and accompanying drawings, in which:

BRIEF DESCRIPTION OF THE DRAWINGS

FIGS. 3-8 are the schematic diagrams showing the flowcharts of the methods for operating the measurements for the sample on the electrochemical test strip in some embodiments of the present invention;

DETAILED DESCRIPTION OF THE PREFERRED EMBODIMENT

The present invention will now be described more specifically with reference to the following embodiments. It is to be noted that the following descriptions of preferred embodiments of this invention are presented herein for the purposes of illustration and description only; it is not intended to be exhaustive or to be limited to the precise form disclosed.

For the competitive relationship between the reaction with the oxygen and that with the mediator, the present invention provides a solution to reduce the oxygen interference. In addition, the present invention is able to sustain steady and accurate working area of the electrodes to raise the accuracy of the measurement. The present invention provides a test strip and a meter to allow the time in the incubation period and test period to be accurately calculated. Besides, the application of the voltage in the interference-removal period is introduced so that the measured current during the test period would not be interfered by the interference materials so as to raise the accuracy of the analyte measurement.

Figure 1:
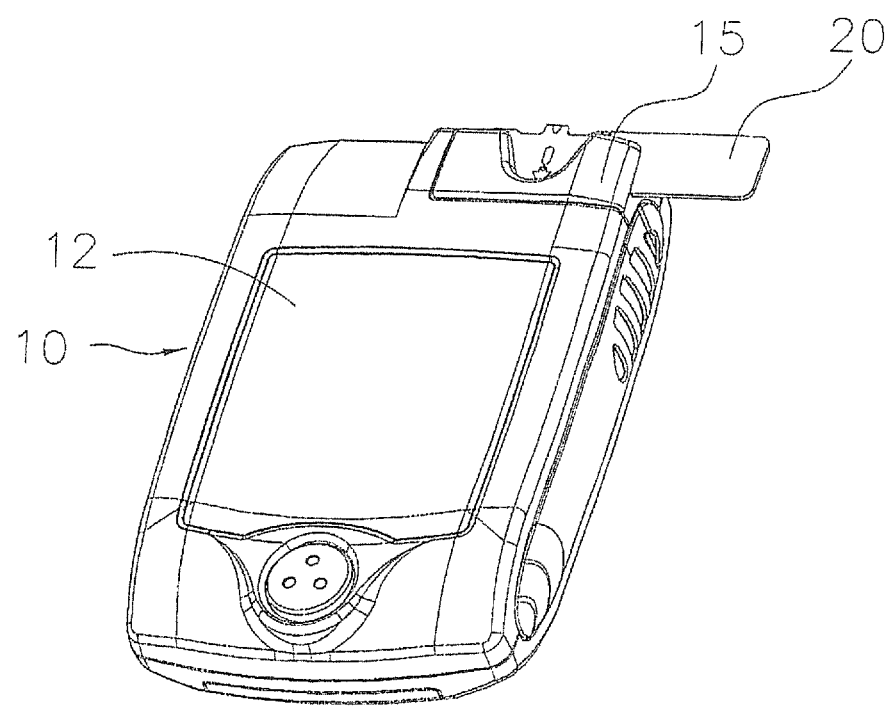
FIG. 1 is the schematic diagram showing a meter with an electrochemical test strip in one embodiment of the present invention.

FIG. 1 shows a meter 10 in one embodiment of the present invention. The meter 10 includes a display device 12 to display the measurement result. The meter 10 includes a slot 15 for the insertion of an electrochemical test strip 20, which is illustrated in details in FIGS. 2A-2D.

Figure 2A:
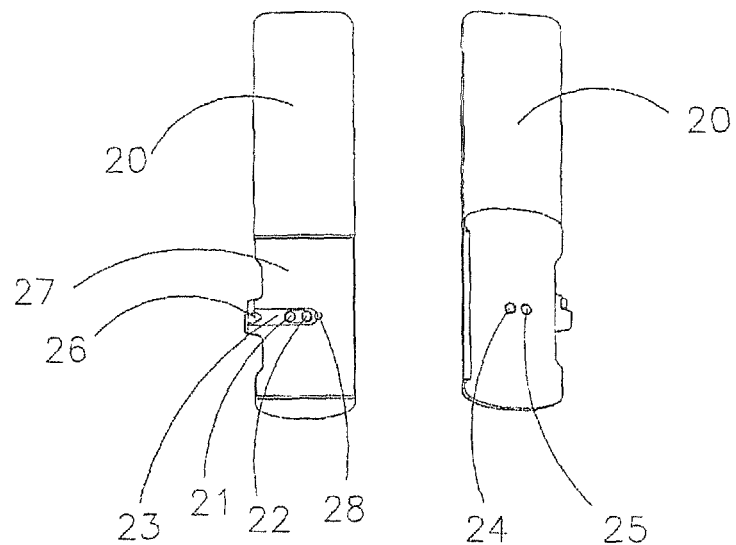
FIG. 2A is the schematic diagram showing a front side and a back side of the electrochemical test strip in one embodiment of the present invention.
Figure 2B:
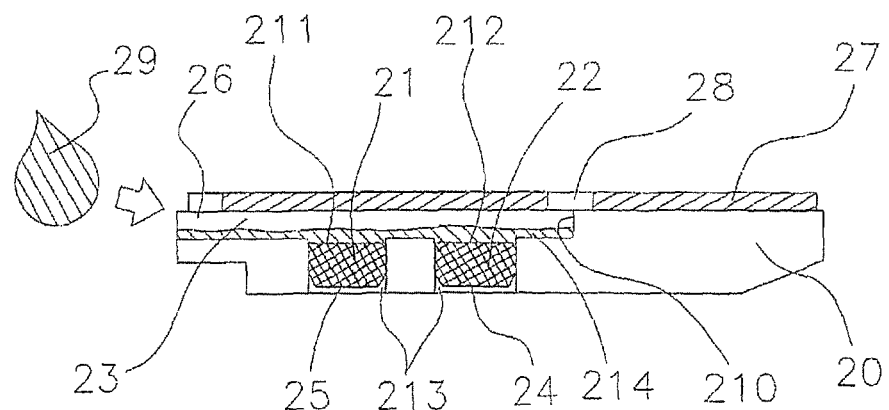
FIG. 2B is the schematic diagram showing a cross sectional view of the electrochemical test strip.

The left diagram of FIG. 2A shows a front side of the electrochemical test strip 20; while the right diagram shows a back side thereof. FIG. 2B shows a cross sectional view of the electrochemical test strip 20 of FIG. 2A.

The electrodes 21 and 22 are disposed in the through holes 213 inside the recess 210 of the electrochemical test strip 20. The peripheral areas of the electrodes 21 and 22 are tightly surrounded by the through holes 213 without any gap therebetween. The diameter of the through holes 213 is designed to be slightly larger than those of the electrodes 21 and 22 such that the electrodes 21 and 22 are mechanically held in the through holes 213.

The upper surfaces 211 and 212 of the electrodes 21 and 22 form the working areas of the electrodes. The lower ends 24 and 25 of the electrodes 21 and 22 form output contacts of the test strip.

A hydrophilic cover 27 with an open hole 28 covers the recess 210 to form a capillary channel 23. The capillary channel 23 defines a reaction zone. In the reaction zone, a reagent 214 is coated in the recess 210 and covers the upper surfaces 211 and 212 of the electrodes 21 and 22. The reagent 214 includes a known enzyme, e.g. a glucose oxidase enzyme, a mediator, e.g. potassium ferricyanide, and some hydrophilic chemical substances. The composition of the reagent is known in the art and is not an essence of the present inventive concept. The test strip 20 is furthermore provided with a sample inlet 26 for filling a liquid sample 29, e.g. a droplet of blood.

Figure 2C:
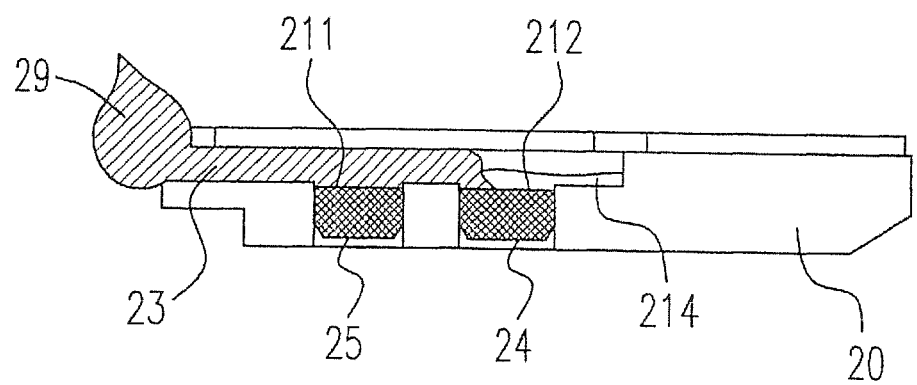
FIGS. 2C and 2D are the schematic diagrams showing the entrance of the sample into the electrochemical test strip of FIG. 2B.
Figure 2D:
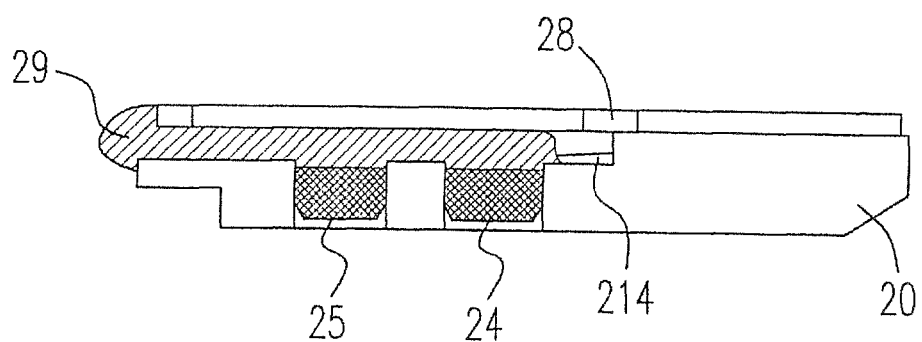

When a blood sample 29 is placed onto an opening of the sample inlet 26 (see FIG. 2C), the droplet is automatically sucked into the capillary channel 23 by capillary action or hydrophilic action. FIGS. 2C and 2D show the flow of the blood sample 29. When dropped to the inlet 26 of the test strip, the sample 29 begins to flow through the capillary channel 23 (see FIG. 2C), till completely covering the electrodes (see FIG. 2D). The air contained in the capillary channel 23 is discharged through the opening 28.

Figure 3:
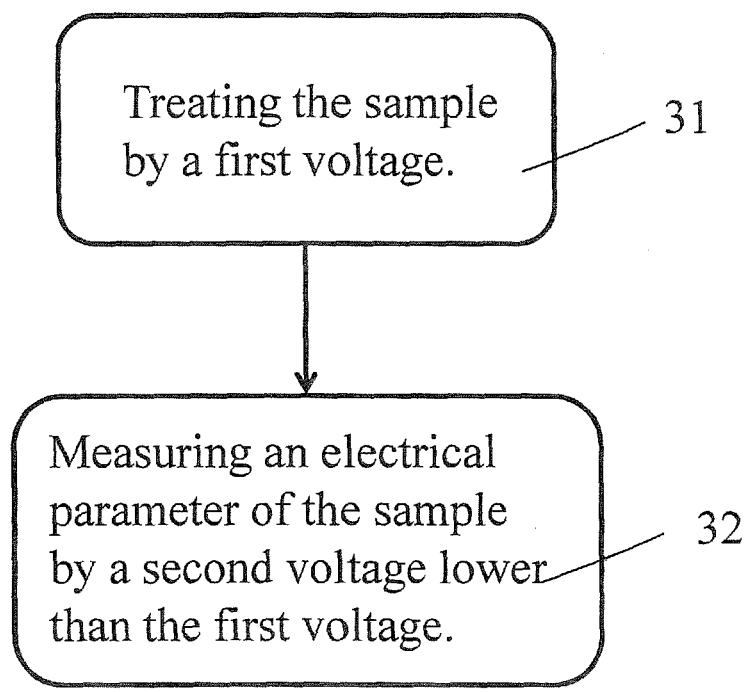

In one embodiment, the method for operating a measurement for a sample is illustrated in FIG. 3 as treating the sample by a first voltage in the step 31 and measuring an electrical parameter of the sample by a second voltage lower than the first voltage in the step 32. The first voltage can oxidize the interference material possibly existing in the sample to effectively reduce the noise from the interference material and to reduce the background noise, that is, to increase the signal-to-noise (S/N) ratio so as to raise the accuracy of the analyte measurement. In this embodiment, the sample includes a blood sample.

The above electrical parameter can include the measured electrical current between the two electrodes, e.g. the electrodes 21 and 22 in FIG. 2A, on the electrochemical test strip. The measured electrical current and the analyte concentration of the sample have a mathematical linear relationship in a measuring domain. The analyte concentration can be calculated from the measured current. The mathematical relationship between the analyte concentration and the measured current can be referred to the above mentioned Cottrell current equation. The above first voltage can be in a range of 0.15-1 voltage, and the above second voltage can be in a range of 0.1-0.9 volt. The first voltage can be a fixed voltage or a set of pulse voltages, and the second voltage can be a fixed voltage. The first voltage can be applied for 0.1-1 s, and the second voltage can be applied for 0.2-10 s. The analyte concentration in this embodiment includes a blood sugar concentration.

The measuring circuit can be power off to result in an open-circuit state, or the applied voltage between the two electrodes can be reduced to zero, during a transition interval between applying the first voltage and the second voltage. Either one of the above two operations lasts for 0.01-0.5 s. That is, the time interval between applying the first voltage and applying the second voltage is in a range of 0.01-0.5 s.

Figure 4:
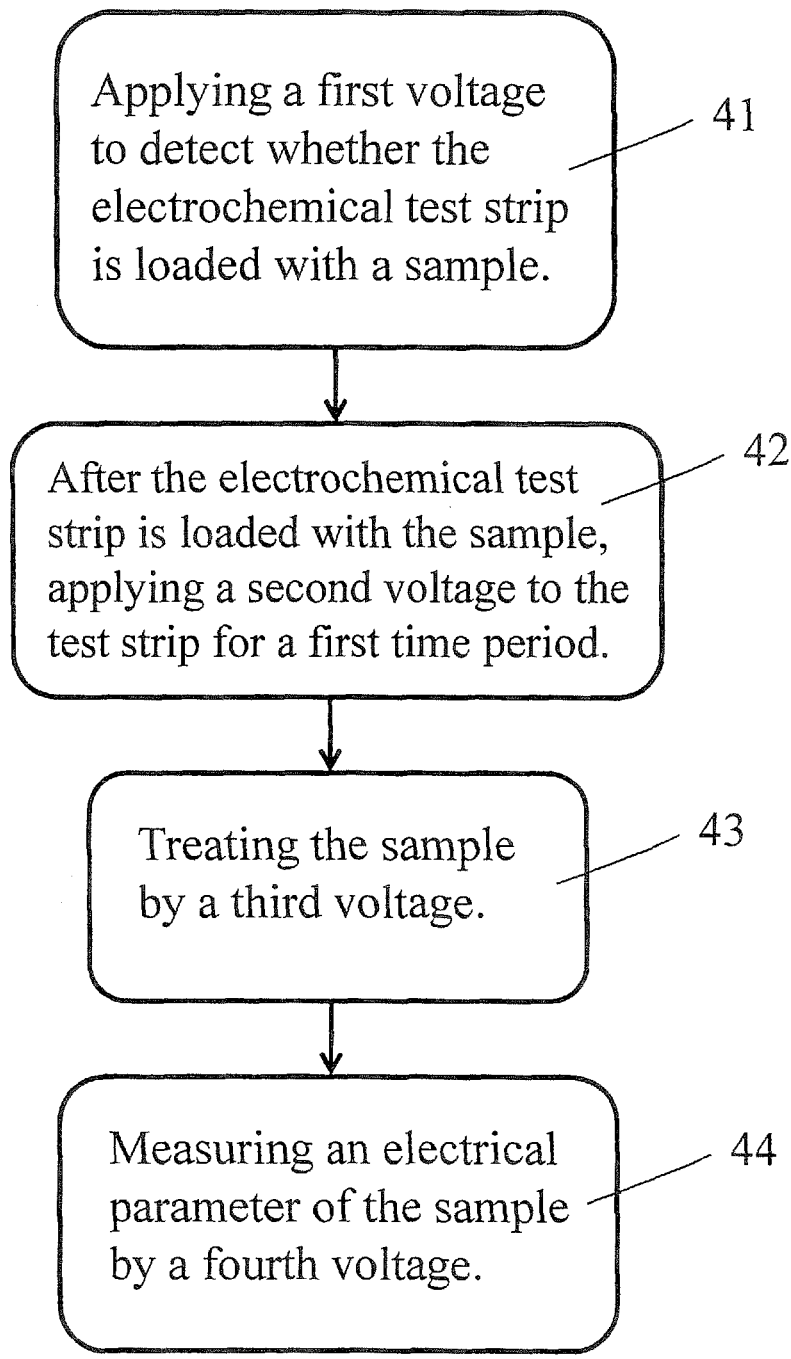

In another embodiment, the method for operating a measurement for a sample is illustrated in FIG. 4 as applying a first voltage to detect whether the electrochemical test strip is loaded with a sample in the step 41, after the electrochemical test strip is loaded with the sample, applying a second voltage to the test strip for a first time period in the step 42, treating the sample by a third voltage in the step 43, and measuring an electrical parameter of the sample by a fourth voltage. In this embodiment, the third voltage can oxidize the interference material possibly existing in the sample to effectively reduce the noise from the interference material and to reduce the background noise, that is, to increase the S/N ratio so as to raise the accuracy of the analyte measurement.

The above electrical parameter in this embodiment can include the measured electrical current between the two electrodes, e.g. the electrodes 21 and 22 in FIG. 2A, on the electrochemical test strip. The measured electrical current and the analyte concentration of the sample have a mathematical linear relationship in a measuring domain. The analyte concentration can be calculated from the measured current. The mathematical relationship between the analyte concentration and the measured current can be referred to the above mentioned Cottrell current equation.

In this embodiment, the first voltage can optionally be a set of plural pulse voltages, and the second voltage with zero or larger than zero volt can optionally be a fixed voltage or a set of plural pulse voltages. The sample in this embodiment can include a blood sample, and the analyte concentration can include a blood sugar concentration.

In this embodiment, the third voltage can optionally be a fixed voltage or a set of plural voltages, the fourth voltage can optionally be a fixed voltage, and the third voltage can be larger than the fourth voltage. The third voltage can be in a range of 0.15-1 volt, and the fourth voltage can be in a range of 0.1-0.9 volt. The third voltage can be applied for 0.1-1 s, ad the fourth voltage can be applied for 0.2-10 s. The measuring circuit can be power off to result in an open-circuit state, or the applied voltage between the two electrodes can be reduced to zero during a transition interval between applying the third voltage and the fourth voltage. Either one of the above two operations lasts for 0.01-0.5 s. That is, the time interval between applying the third voltage and applying the fourth voltage is in a range of 0.01-0.5 s.

Figure 5:
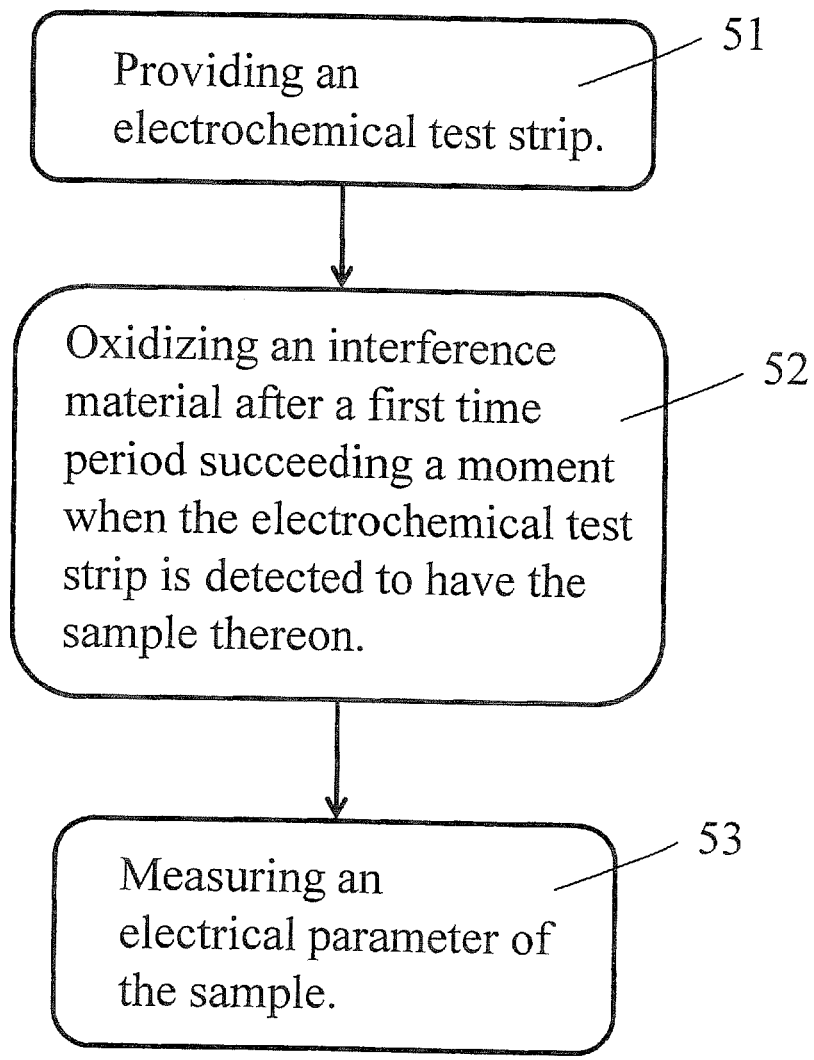

In another embodiment, the method for operating a measurement for a sample is illustrated in FIG. 5 as providing an electrochemical test strip in the step 51, oxidizing an interference material after a first time period succeeding a moment when the electrochemical test strip is detected to have the sample thereon in the step 52, and measuring an electrical parameter of the sample in the step 53. In this embodiment, the step of oxidizing the interference material can be performed by optionally applying a voltage, which is higher than that applied to measure the electrical parameter and can be a fixed voltage or a set of plural pulse voltages, to effectively reduce the noise from the interference material and to reduce the background noise, that is, to increase the S/N ratio so as to raise the accuracy of the analyte measurement.

Similarly, the above electrical parameter in this embodiment can include the measured electrical current between the two electrodes, e.g. the electrodes 21 and 22 in FIG. 2A, on the electrochemical test strip. The measured electrical current and the analyte concentration of the sample have a mathematical linear relationship in a measuring domain. The analyte concentration can be calculated from the measured current. The mathematical relationship between the analyte concentration and the measured current can be referred to the above mentioned Cottrell current equation. The sample in this embodiment can include a blood sample, and the analyte concentration can include a blood sugar concentration.

Figure 6:
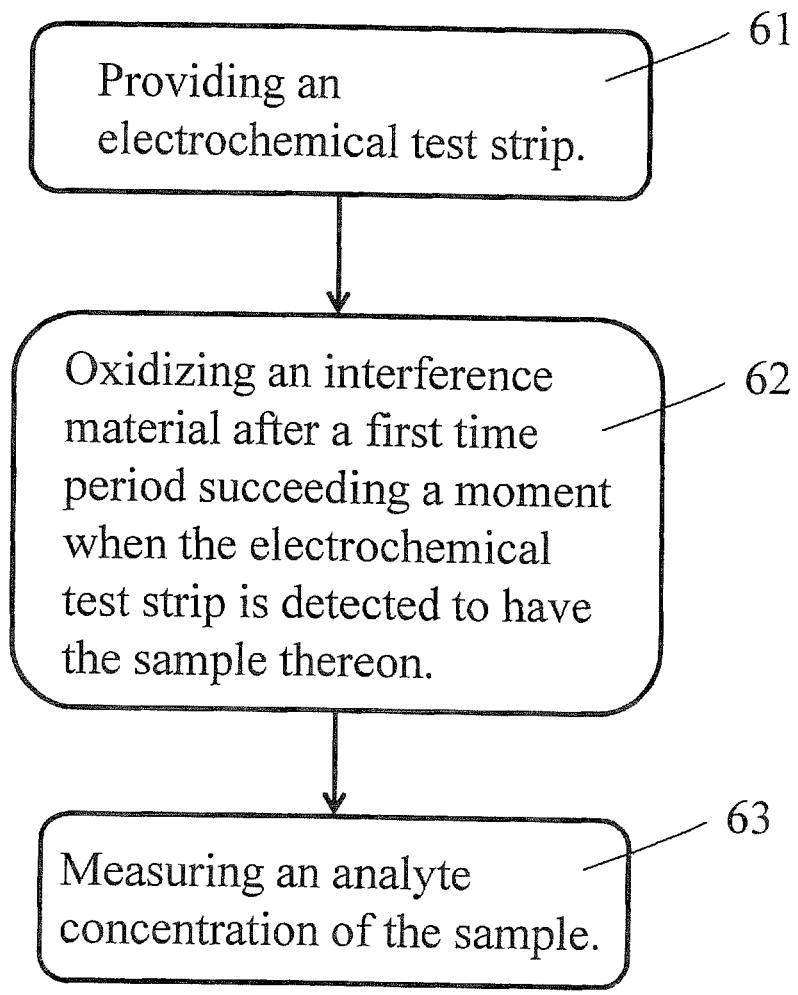

In another embodiment, the method for operating a measurement for a sample is illustrated in FIG. 6 as providing an electrochemical test strip in the step 61, oxidizing an interference material after a first time period succeeding a moment when the electrochemical test strip is detected to have the sample thereon in the step 62, and measuring an analyte concentration of the sample in the step 63. Similarly, in this embodiment, the step of oxidizing the interference material can be performed by optionally applying a voltage, which is higher than that applied to measure the analyte concentration and can be a fixed voltage or a set of plural pulse voltages, to oxidizing the interference material possibly existing in the sample, to effectively reduce the noise from the interference material and to reduce the background noise, that is, to increase the S/N ratio so as to raise the accuracy of the analyte measurement. The sample in this embodiment can include a blood sample, and the analyte concentration can include a blood sugar concentration.

In another embodiment, the method for operating a measurement for a sample is illustrated in FIG. 7 as applying a first voltage between the two electrodes during an interference-removal period after an incubation period succeeding a moment when the sample is detected in the step 71, and applying a second voltage between the two electrodes during a test period in the step 72, wherein the first voltage is larger than the second voltage, the first voltage can be a fixed voltage or a set of plural pulse voltages, and the second voltage can be a fixed voltage. Similarly, in this embodiment, the application of the first voltage can oxidize the interference material to effectively reduce the noise from the interference material and to reduce the background noise, that is, to increase the S/N ratio so as to raise the accuracy of the analyte measurement. The sample in this embodiment can include a blood sample, and the measured property in the test period can include a blood sugar concentration in the blood sample.

Figure 8:
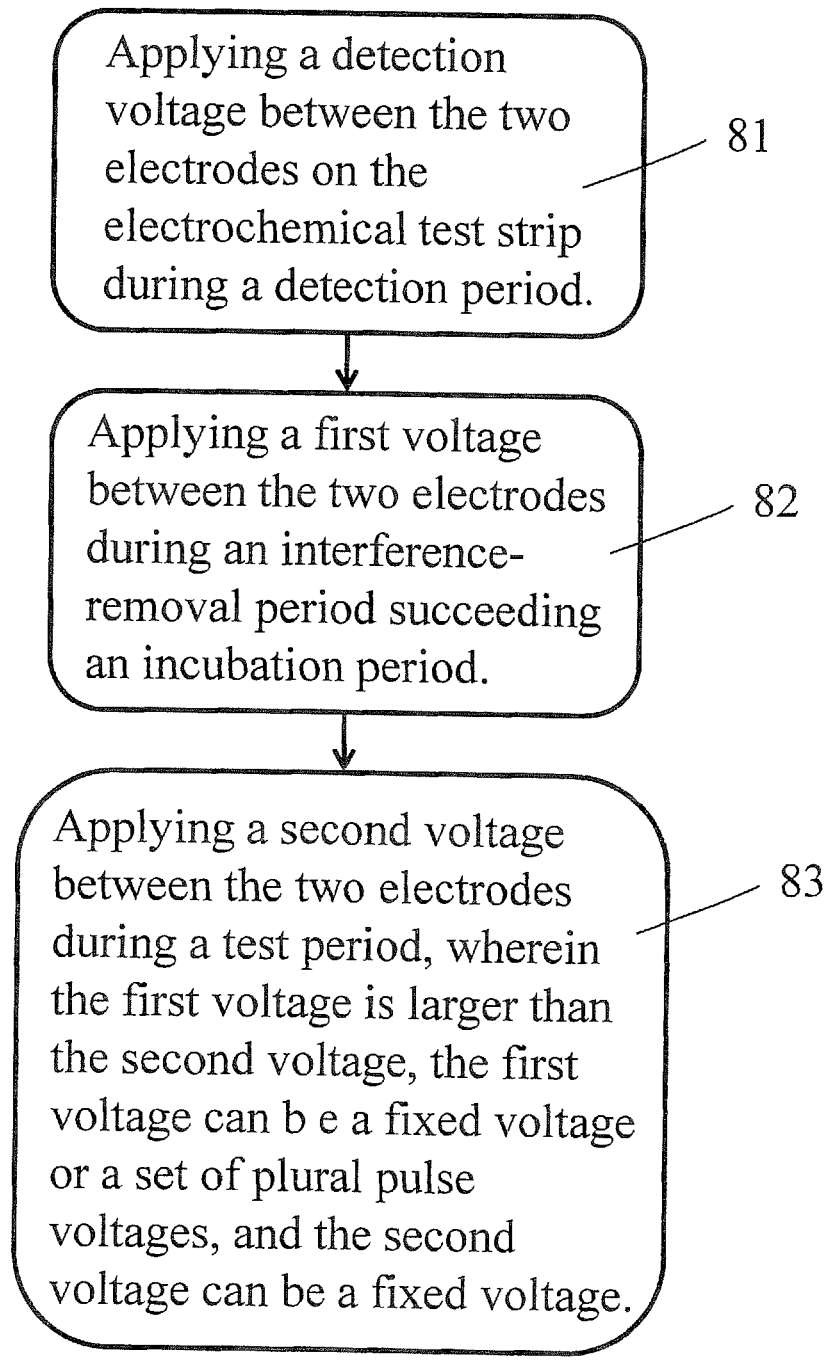

In another embodiment, the method for operating a measurement for a sample is illustrated in FIG. 8 as applying a detection voltage between the two electrodes on the electrochemical test strip during a detection period in the step 81, applying a first voltage between the two electrodes during an interference-removal period succeeding an incubation period in the step 82, and applying a second voltage between the two electrodes during a test period in the step 83, wherein the first voltage is larger than the second voltage, the first voltage can be a fixed voltage or a set of plural pulse voltages, and the second voltage can be a fixed voltage. In this embodiment, the application of the first voltage between the two electrodes during the interference-removal period can oxidize the interference material possibly existing in the sample to effectively reduce the noise from the interference material and to reduce the background noise, that is, to increase the S/N ratio so as to raise the accuracy of the analyte measurement. The sample in this embodiment can include a blood sample, and the measured property in the test period can include a blood sugar concentration in the blood sample.

The above first electrode can be in a range of 0.15-1 volt, preferably 0.3-0.4 volt, and the above second electrode can be in a range of 0.1-0.9 volt, preferably 0.15-0.25 volt. The above first voltage can be applied for 0.1-1 s, preferably 0.4-0.6 s, and the above second voltage can be applied for 0.2-10 s, preferably 1-2 s. In this embodiment, the first voltage with 0.35 volt is applied for 0.5 s, and the second voltage with 0.2 volt is applied for 1.3 s.

In some embodiments of the present invention, the detection voltage is applied between the two electrodes during the sample presence detection period till the sample is detected. The detection voltage can optionally be a detection set of plural pulse voltages, each of which can be in a range of 0.1-0.5 volt, preferably 0.15-0.25 volt. Each pulse of the detection set of plural pulse voltages has a detection pulse width in a range of 100-600 µs, preferably 300-400 µs. The detection set of plural pulse voltages has a detection pulse interval between two adjacent pulses therein, where the detection pulse interval is in a range of 10-50 ms, preferably 15-25 ms. In an embodiment of the present invention, each of the detection set of plural pulse voltages is 0.2 volt, the detection pulse width is 350 µs, and the detection pulse interval is 20 ms.

In an embodiment, when a detected electrical current between the two electrodes is larger than a predetermined threshold, the sample is deemed as being detected, and the sample presence detection period is ended.

In some of embodiments of the preset invention, an incubation voltage applied during the incubation period is high enough to oxidize the mediator inside the reagent on the electrochemical test strip from a reduction state to an oxidation state and is low enough to avoid oxidizing the hydrogen peroxide inside the reagent. The incubation voltage is in a range of 0.10-0.68 volt. In some embodiments, the incubation voltage can optionally be an incubation set of plural pulse voltages, each of which can be in a range of 0.1-0.6 volt, preferably 0.15-0.25 volt. Each pulse of the incubation set of plural pulse voltages can have an incubation pulse width in a range of 100-500 µs, preferably 150-250 µs. The incubation set of plural pulse voltages has an incubation pulse interval between two adjacent pulses therein, and the incubation pulse interval is in a range of 100-500 ms, preferably 150-250 ms. In one embodiment, each of the incubation set of plural pulse voltages can be 0.2 volt, the incubation pulse width can be 200 µs, and the incubation pulse interval can be 200 ms. The above application of the incubation voltage can effectively facilitate the mixing and the reaction between the reagent and the sample, can reduce the mixing time, can shorten the total time for the application of the voltages when cooperated with the application of the interference-removal voltage, and can raise the accuracy of the measurement.

In some embodiments, one of the two following operations can be optionally performed between the interference-removal period and the test period: (1) causing a power-off to result in an open-circuit state in a measuring circuit, and (2) applying a zero voltage between the two electrodes. The operation time for either one of the above two operations can be in a range of 0.01-0.5 s, e.g. 0.05, 0.1, 0.2, 0.3 s, etc.

In some embodiments, there are the reagent and the mediator on the electrochemical test strip. The reagent can include glucose oxidase enzyme, and the mediator can include potassium ferricyanide to undergo the reactions shown in the above chemical equations (1)-(3). The measured electrical current between two electrodes on the electrochemical test strip during the test period can be measured, and the blood sugar concentration in the blood sample can be accurately calculated by applying the above Cottrell current equation.

Figure 9:
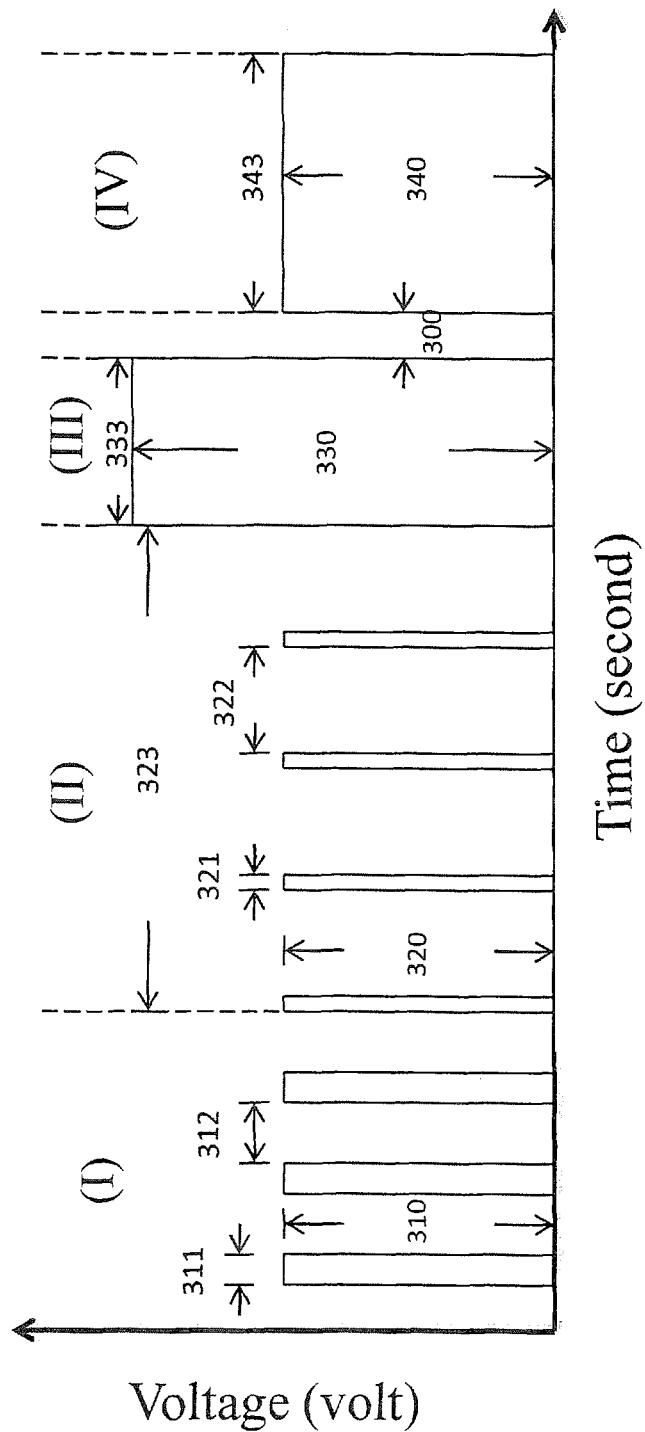
FIG. 9 is the schematic diagram showing a relationship between the applied voltage and operation time during each period of the measurement for a sample, by using an electrochemical test strip in one embodiment of the present invention.

Refer to FIG. 9, which shows a relationship between the applied voltage and operation time during each period of the measurement for a sample, by using an electrochemical test strip in one embodiment of the present invention. It is noted that for clarity, the time periods and time intervals in FIG. 9 are not drawn according to the proportional scale, since the pulse width is smaller than one thousandth of the pulse interval between two adjacent pulses in the stage (II). The pulse width in the stage (II) cannot be clearly recognized, if FIG. 9 is drawn according to the proportional scale. As shown in FIG. 9, in the stage (I), i.e. the sample presence detection period, plural pulses with the voltage 310 of 0.2 volt are applied, the pulse width 311 of each pulse can be 350 µs, and the pulse interval 312 between two adjacent pulses can be 20 ms. When the measured electrical current between the two electrodes on the electrochemical test strip is higher than a predetermined threshold, the sample is deemed as being detected and the detection period is ended. In the following stage (II), i.e. the incubation period, plural pulse voltages or no voltage at all can be optionally applied. If plural pulse voltages are applied in the stage (II), the voltage 320 can be 0.2 volt, the pulse width 321 can be 200 µs, and the pulse interval 322 between two adjacent pulses can be 200 ms. The incubation period 323 lasts for about 2 s. In the following stage (III), i.e. the interference-removal period, a fixed voltage 330 of 0.35 volt is applied, and the time width 333 lasts for about 0.5 s. In the following stage (IV), i.e. test period, a fixed voltage 340 of 0.2 volt is applied, the time period 343 of the test period lasts for about 1.3 s, and the data, i.e. the measured current between the two electrodes on the electrochemical test strip, starts to be collected after 0.3 s past the initiation of the test period so as to calculate the blood sugar concentration in the blood sample. In a transition interval between the interference-removal period and the test period, one of the two following operations can be optionally performed: 1) causing the measuring circuit to be powered off to result in an open-circuit state, and (2) applying a zero voltage between the two electrodes. The operation time period 300 for either one of the above two operations can be 0.1 s. Since the interference-removal period is specially introduced in this embodiment by applying the fixed voltage of 0.35 volt, the interference material possibly existing in the sample can be oxidized before the initiation of the measurements so that the background noise in the measurements can be reduced and the measurement accuracy of the blood sugar concentration can be significantly raised.

Figure 10:
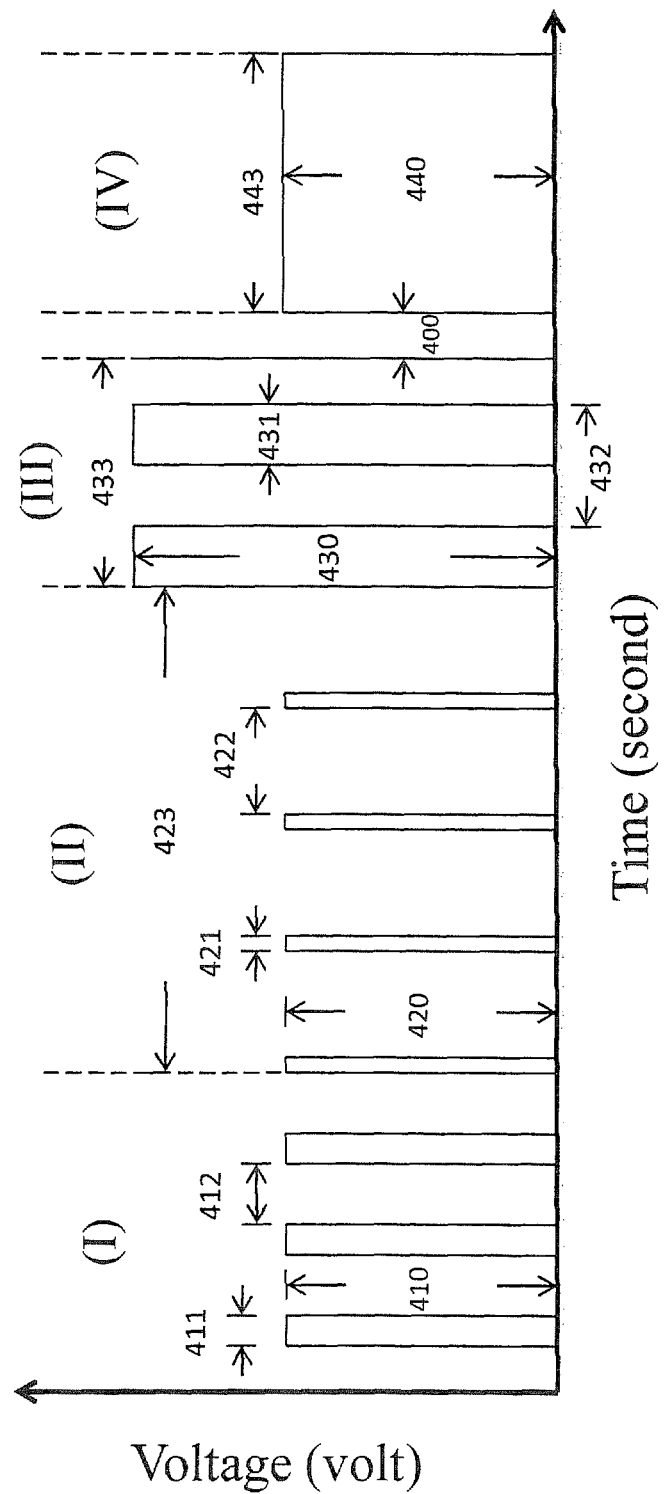
FIG. 10 is the schematic diagram showing a relationship between the applied voltage and operation time during each period of the measurement for a sample, by using an electrochemical test strip in another embodiment of the present invention.

Refer to FIG. 10, which shows a relationship between the applied voltage and operation time during each period of the measurement for a sample, by using an electrochemical test strip in another embodiment of the present invention. Similarly, for clarity, the time widths and time intervals in various stages in FIG. 10 are not drawn according to the proportional scale. As shown in FIG. 10, in the stage (I), i.e. the detection period, plural pulses with the voltage 410 of 0.2 volt are applied, the pulse width 411 of each pulse can be 350 µm, and the time interval 412 between two adjacent pulses can be 20 ms. The pulses in the stage (I) are continuously applied until the electrical current between the two electrodes on the electrochemical test strip is higher than a predetermined threshold, that is, the sample is deemed as being detected and the detection period is ended. In the following stage (II), i.e. incubation period, plural pulses or no voltage at all can be optionally applied. When plural pulses are applied, the voltage 420 of each of the plural pulse can be 0.2 volt, the pulse width 421 of each pulse can be 200 µs, and the pulse interval 422, i.e. the time interval between two adjacent pulses, can be 200 ms. The time period 423 of the incubation period lasts for about 2 s. In the following stage (III), i.e. the interference-removal period, plural pulses with the voltage 430 of 0.35 volt are applied, the pulse width 431 of each pulse can be 125 ms, and the pulse interval, i.e. the time interval between two adjacent pulses, can be 125 ms. The time period 433 of the interference-removal period lasts for about 0.5 s. In the following stage (IV), i.e. the test period, a fixed voltage 440 of 0.2 volt is applied, and the time period 443 of the test period lasts for about 1.3 s, and the data, i.e. the measured current between the two electrodes on the electrochemical test strip, starts to be collected after 0.3 s past the initiation of the test period so as to calculate the blood sugar concentration in the blood sample. In a transition interval between the interference-removal period and the test period, one of the two following operations can be optionally performed: 1) causing the measuring circuit to be powered off to result in an open-circuit state, and (2) applying a zero voltage between the two electrodes. The operation time period 400 for the above two operations can be 0.1 s. Since the interference-removal period is specially introduced in this embodiment by applying the plural pulse voltages of 0.35 volt, the interference material possibly existing in the sample can be oxidized before the initiation of the measurements so that the background noise in the measurements can be reduced and the measurement accuracy of the blood sugar concentration can be significantly raised.

Of course, based on the concept of the present invention, the voltages of the plural pulses, the time interval between two adjacent pulses and the entire time period in the stage (III), i.e. the interference-removal period, in FIG. 10 can be appropriately adjusted based on the practical requirements. For instance, the voltage of each of the plural pulses can be in a range of 0.15-1 volt, the pulse interval, i.e. the time interval between two adjacent pulses can be in a range of 5-100 ms, and the entire period of the interference-removal period can be in a range of 0.1-1 s.

Figure 11:
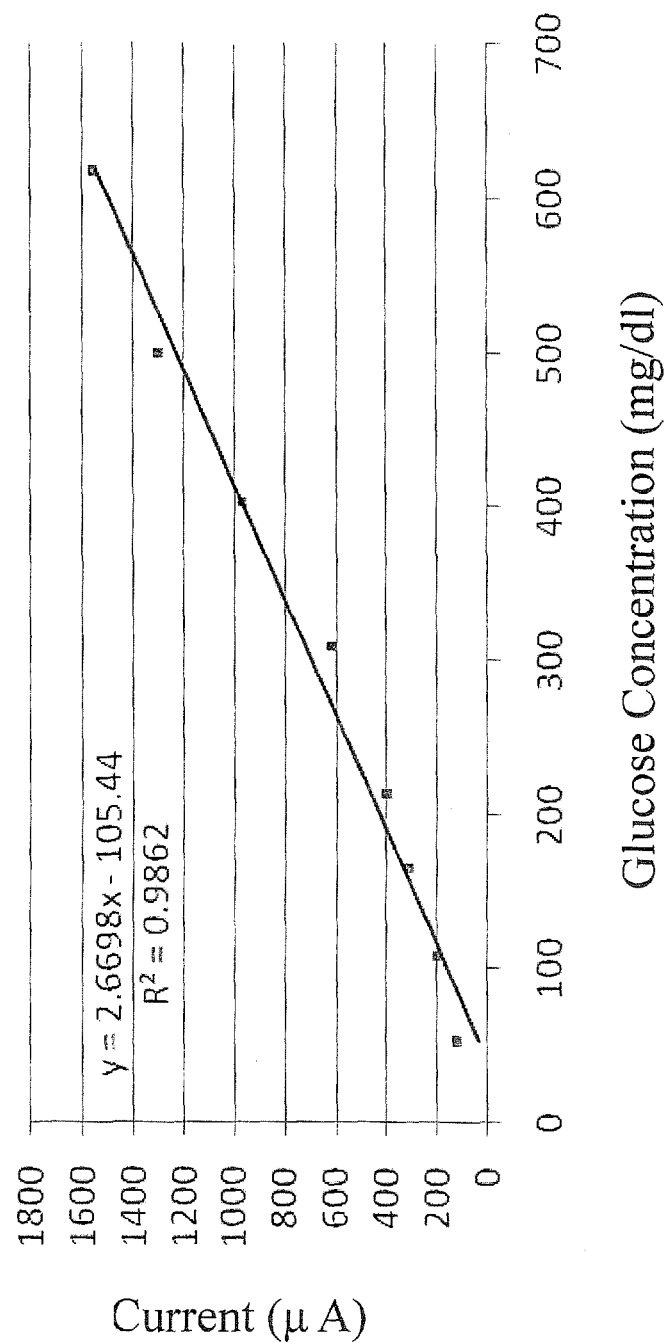
FIG. 11 is the schematic diagram showing a relationship between the measured electrical current through the sample and the glucose concentration during the test period without introducing the interference-removal period, by using an electrochemical test strip.
Figure 12:
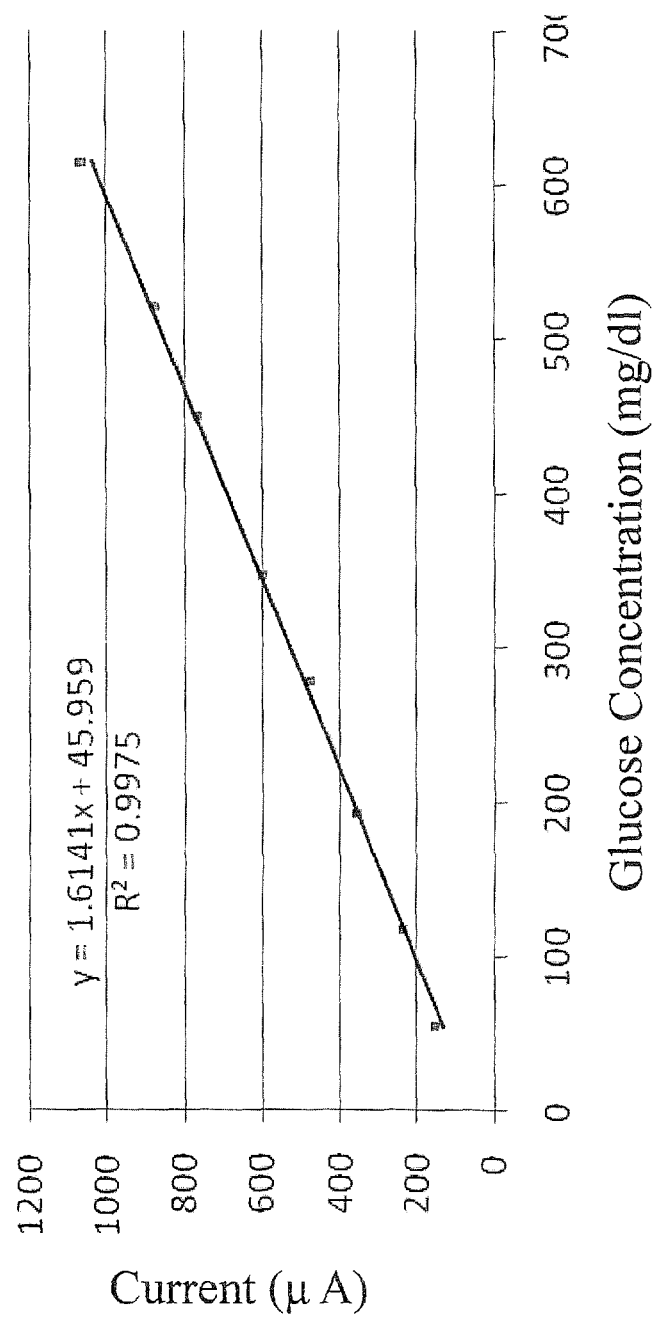
FIG. 12 is the schematic diagram showing a relationship between the measured electrical current through the sample and the glucose concentration during the test period after the application of a high fixed voltage in the interference-removal period, by using an electrochemical test strip in one embodiment of the present invention.

FIG. 11 shows a relationship between the measured electrical current through the sample and the glucose concentration during the test period without introducing the interference-removal period, by using an electrochemical test strip in a conventional technique. FIG. 12 shows a relationship between the measured electrical current through the sample and the glucose concentration during the test period after the introduction of high fixed voltage, 0.35 volt, in the interference-removal period, by using an electrochemical test strip in one embodiment of the present invention. As shown in FIG. 11, the $R^2$, the coefficient of determination indicating goodness-of-fit of the regression, is equal to 0.9862, that is, the linear relationship of the measured data in the test period is not good enough in the conventional technique, and there are several data points located at a distance away from the linear regression line, since no interference-removal period is introduced.

In FIG. 12, the interference-removal period is introduced by continuously applying the fixed voltage of 0.35 volt for 0.5 s, then the above power-off action or the application of zero voltage is performed for 0.1 s, and after then the measurement proceeds in the test period. The measurement conditions in the test period in FIG. 12 are completely the same as those in FIG. 11. As shown in FIG. 12, the $R^2$ is equal to 0.9975 and almost all the data points are located in contact with the linear regression line with excellent linear relationship for the measured data. It can be known after the comparison of FIGS. 11 and 12 that the introduction of the interference-removal period by applying the fixed voltage of 0.35 volt higher than the voltage of 0.2 volt applied in the test period can oxidize the interference material before the initiation of the test period, so that the measured electrical current in the test period would not be interfered by the interference material, the background noise in the measurements can be effectively reduced, that is, the signal/noise (S/N) ratio can be increased, and accordingly better linear relationship for the measured data can be successfully obtained with the measurement accuracy significantly improved for the analyte, e.g. blood sugar concentration.

Figure 13:
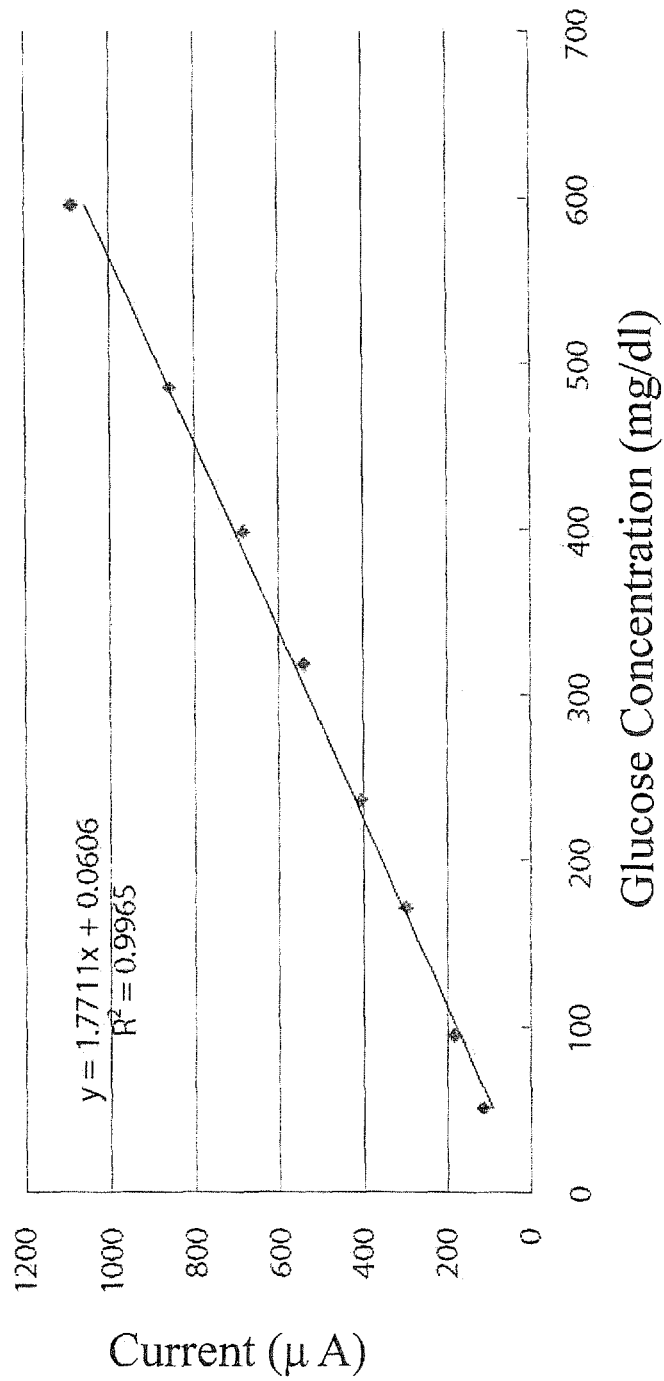
FIG. 13 is the schematic diagram showing a relationship between the measured electrical current through the sample and the glucose concentration during the test period after the application of high pulse voltages in the interference-removal period, by using an electrochemical test strip in one embodiment of the present invention.

In FIG. 13, the interference-removal period proposed in the present invention is also introduced, where plural pulse voltages of 0.35 volt are applied, this interference-removal period lasts for 0.5 s, then the above power-off action or the application of zero voltage is performed for 0.1 s, and after then the measurement proceeds in the test period. The measurement conditions in the test period in FIG. 13 are completely the same as in FIG. 12. As shown in FIG. 13, the $R^2$ is equal to 0.9965 and almost all the data points are located in contact with the linear regression line with excellent linear relationship for the measured data. It can be understood after the comparison of FIGS. 11 and 13 that the introduction of the interference-removal period by applying the plural pulse voltages of 0.35 volt higher than the voltage of 0.2 volt applied in the test period can oxidize the interference material before the initiation of the test period, so that the measured electrical current in the test period would not be interfered by the interference material, the background noise in the measurements can be effectively reduced, that is, the S/N ratio can be increased, and accordingly better linear relationship for the measured data can be successfully obtained with the measurement accuracy significantly improved for the analyte, e.g. blood sugar concentration.

Some embodiments of the present invention are described in the followings.

1. A method for operating a measurement for a sample on an electrochemical test strip including at least two electrodes is provided. The method includes steps of applying a first voltage between the two electrodes during an interference-removal period after an incubation period succeeding a moment when the sample is detected; and applying a second voltage between the two electrodes during a test period, wherein the first voltage is larger than the second voltage, the first voltage includes one of a first fixed voltage and a first set of plural pulse voltages, and the second voltage includes a second fixed voltage.
2. A method of Embodiment 1 further includes a step of applying a detection voltage between the two electrodes during a sample presence detection period before the step of applying the first voltage.
3. In a method of any one of the above embodiments, the first voltage is in a range of 0.3-0.4 volt; the second voltage is in a range of 0.15-0.25 volt; the first applying period is in a range of 0.4-0.6 s; the second applying period is in a range of 1-2 s; and the step of applying the second voltage is performed to measure a blood sugar concentration of the sample.
4. A method of any one of the above embodiments further includes a step of, during a transition interval between the interference-removal period and the test period, wherein the transition interval lasts for 0.01-0.5 s, performing one of following operations: causing a power-off to result in an open-circuit state in a measuring circuit; and applying a zero voltage between the two electrodes.
5. A method for operating a measurement for a sample on an electrochemical test strip is provided, wherein the sample includes an interference material and an analyte concentration, and the method includes steps of providing the electrochemical test strip; oxidizing the interference material after a first time period succeeding a moment when the electrochemical test strip is detected to have the sample thereon; and measuring the analyte concentration.
6. In a method of any one of the above embodiments, the electrochemical test strip includes at least two electrodes, and the method further includes a step of applying a detection voltage between the two electrodes during a sample presence detection period before the step of oxidizing the interference material.

7. In a method of any one of the above embodiments, the step of applying the detection voltage continues till the sample is detected; when a detected electrical current between the two electrodes is higher than a threshold, the sample is deemed as being detected, and the sample presence detection period is ended; the detection voltage includes a detection set of plural pulse voltages, each of which is in a range of 0.1-0.5 volt; each pulse of the detection set of plural pulse voltages has a detection pulse width in a range of 100-600 μs; and the detection set of plural pulse voltages has a detection pulse interval between two adjacent pulses therein, wherein the detection pulse interval is in a range of 10-50 ms.

8. In a method of any one of the above embodiments, the sample includes a blood sample; the each voltage of the detection set of plural pulse voltages is in a range of 0.15-0.25 volt; the detection pulse width is in a range of 300-400 μs; and the detection pulse interval is in a range of 15-25 ms.

9. In a method of any one of the above embodiments, the electrochemical test strip includes a hydrogen peroxide and a reagent containing a mediator having a reduction state and an oxidation state, and the method further includes a step of applying an incubation voltage after the sample presence detection period, wherein the incubation voltage is high enough to oxidize the mediator from the reduction state to the oxidation state and is low enough to avoid oxidizing the hydrogen peroxide, wherein the incubation voltage includes an incubation set of plural pulse voltages, each of which is in a range of 0.1-0.6 volt; each pulse of the incubation set of plural pulse voltages has an incubation pulse width in a range of 100-500 μs; and the incubation set of plural pulse voltages has an incubation pulse interval between two adjacent pulses therein, wherein the incubation pulse interval is in a range of 100-500 ms.

10. In a method of any one of the above embodiments, the each voltage of the incubation set of plural pulse voltages is in a range of 0.15-0.25 volt; the incubation pulse width is in a range of 150-250 μs; the incubation pulse interval is in a range of 150-250 ms; the reagent further includes a glucose oxidase enzyme; and the mediator includes a potassium ferrocyanide.

11. In a method of any one of the above embodiments, one of following operations is performed during the incubation period: causing a power-off to result in an open-circuit state in a measuring circuit; and applying a zero voltage between the two electrodes.

12. In a method of any one of the above embodiments, the sample includes a blood sample; the electrochemical test strip includes at least two electrodes; the step of oxidizing the interference material includes applying a first voltage between the two electrodes; the step of measuring the analyte concentration includes applying a second voltage between the two electrodes to measure an electrical parameter; the first voltage is higher than the second voltage; the first voltage includes one of a first fixed voltage and a first set of plural pulse voltages; and the second voltage includes a second fixed voltage.

13. In a method of any one of the above embodiments, the first voltage is in a range of 0.15-1 volt; the second voltage is in a range of 0.1-0.9 volt; the step of applying the first voltage is performed for 0.1-1 s; and the step of applying the second voltage is performed for 0.2-10 s.

14. In a method of any one of the above embodiments, the electrical parameter includes a detected electrical current between the two electrodes; the detected electrical current and the analyte concentration have a mathematical linear relationship in a measuring domain; the analyte concentration is calculated based on the detected electrical current; and the analyte concentration includes a blood sugar concentration.

15. A method of any one of the above embodiments further includes a step of, during a transition interval between the steps of oxidizing the interference material and measuring the analyte concentration, wherein the transition interval lasts 0.01-0.5 s, performing one of following operations: causing a power-off to result in an open-circuit state in a measuring circuit; and applying a zero voltage between the two electrodes.

16. A method for operating a measurement for a sample on an electrochemical test strip including at least two electrodes is provided. The method includes steps of treating the sample by a first voltage; and measuring an electrical parameter of the sample by a second voltage lower than the first voltage.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. A method for operating a measurement for a sample on an electrochemical test strip, wherein the sample includes an interference material and an analyte concentration, the method comprising steps of:
   providing the electrochemical test strip, wherein the electrochemical test strip includes two electrodes, a hydrogen peroxide and a reagent containing a mediator having a reduction state and an oxidation state;
   applying a detection voltage between the two electrodes during a sample presence detection period;
   applying an incubation voltage between the two electrodes during an incubation period succeeding a moment when the electrochemical test strip is detected to have the sample thereon, wherein:
   the incubation voltage has a maximum voltage value,
   the maximum voltage value is high enough to oxidize the mediator from the reduction state to the oxidation state and is low enough to avoid oxidizing the hydrogen peroxide,
   the incubation voltage includes an incubation set of plural pulse voltages, each of which is in a range of 0.1-0.6 volt,
   each pulse of the incubation set of plural pulse voltages has an incubation pulse width in a range of 100-500 μs, and
   the incubation set of plural pulse voltages has an incubation pulse interval between two adjacent pulses therein, wherein the incubation pulse interval is in a range of 100-500 ms;
   oxidizing the interference material by applying a first voltage between the two electrodes during an interference-removal period after the incubation period, wherein the first voltage includes one of a first fixed voltage and a first set of plural pulse voltages and is in a range of 0.15-1 volt, and the first voltage is applied for 0.1-1 s;

measuring the analyte concentration by applying a second voltage between the two electrodes during a test period, wherein the first voltage is higher than the second voltage, the second voltage includes a second fixed voltage and is in a range of 0.1-0.9 volt, and the second voltage is applied for 0.2-10 s; and during a transition interval between the interference-removal period and the test period, performing one of following operations:

causing a power-off to result in an open-circuit state in a measuring circuit; and applying a zero voltage between the two electrodes, wherein the transition interval lasts 0.01-0.5 s.

2. A method of claim 1, wherein the step of applying the detection voltage continues till the sample is detected;

when a detected electrical current between the two electrodes is higher than a threshold, the electrochemical test strip is deemed to have the sample thereon, and the sample presence detection period is ended;

the detection voltage includes a detection set of plural pulse voltages, each of which is in a range of 0.1-0.5 volt;

each pulse of the detection set of plural pulse voltages has a detection pulse width in a range of 100-600 µs; and the detection set of plural pulse voltages has a detection pulse interval between two adjacent pulses therein, wherein the detection pulse interval is in a range of 10-50 ms.

3. A method of claim 2, wherein:

the sample includes a blood sample;

the each voltage of the detection set of plural pulse voltages is in a range of 0.15-0.25 volt;

the detection pulse width is in a range of 300-400 µs; and the detection pulse interval is in a range of 15-25 ms.

4. A method of claim 1, wherein:

the each voltage of the incubation set of plural pulse voltages is in a range of 0.15-0.25 volt;

the incubation pulse width is in a range of 150-250 µs;

the incubation pulse interval is in a range of 150-250 ms;

the reagent further includes a glucose oxidase enzyme; and the mediator includes a potassium ferrocyanide.

5. A method of claim 1, wherein:

the sample includes a blood sample; and the second voltage is applied to measure an electrical parameter, thereby measuring the analyte concentration.

6. A method of claim 5, wherein:

the electrical parameter includes a detected electrical current between the two electrodes;

the detected electrical current and the analyte concentration have a mathematical linear relationship in a measuring domain;

the analyte concentration is calculated based on the detected electrical current; and the analyte concentration includes a blood sugar concentration.

* * * * *